US005840290A

United States Patent [19]
Hench et al.

[11] Patent Number: 5,840,290
[45] Date of Patent: Nov. 24, 1998

[54] INJECTABLE BIO-ACTIVE GLASS IN A DEXTRAN SUSPENSION

[75] Inventors: Larry L. Hench, London, England; Jon K. West; Guy LaTorre, both of Gainesville, Fla.; June Wilson, London, England; William Toreki, III, Gainesville, Fla.; Christopher Batich, Gainesville, Fla.

[73] Assignee: University of Florida Research Foundation, Gainesville, Fla.

[21] Appl. No.: 657,713

[22] Filed: May 30, 1996

[51] Int. Cl.$^6$ .............................. A61F 2/02; A61K 9/50; B32B 5/16

[52] U.S. Cl. ........................ 424/423; 424/499; 428/402; 428/402.24

[58] Field of Search ...................... 424/423, 499; 428/402, 402.24; 523/115

[56] References Cited

U.S. PATENT DOCUMENTS

| | | |
|---|---|---|
| 4,103,002 | 7/1978 | Hench et al. . |
| 4,159,358 | 6/1979 | Hench et al. . |
| 4,171,544 | 10/1979 | Hench et al. . |
| 4,189,325 | 2/1980 | Barrett et al. . |
| 4,234,972 | 11/1980 | Hench et al. . |
| 4,775,646 | 10/1988 | Hench et al. . |
| 4,803,075 | 2/1989 | Wallace et al. . |
| 4,851,046 | 7/1989 | Low et al. . |
| 5,074,916 | 12/1991 | Hench et al. . |
| 5,204,382 | 4/1993 | Wallace et al. . |
| 5,352,715 | 10/1994 | Wallace et al. . |
| 5,451,406 | 9/1995 | Lawin et al. ............................ 424/423 |

OTHER PUBLICATIONS

R. Dixon Walker et al., "Injectable Bioglass as a Potential Substitute For Injectable Polytetrafluoroethylene", *The Journal of Urology*, vol. 1, pp. 65–67, Aug. 1992.

Larry L. Hench & June Wilson, "Advanced Series in Ceramics", *An Introduction in Bioceramics*, — v1, pp. 1–24.

Kirk–Othmer, "*Concise Encyclopedia of Chemical Technology*", 1985, pp. 104–106.

John F. Buckley et al., Endoscopic Correction of Vesicoureteric Reflux with Injectable Microparticulate Silicone, "*The Journal of Urology*", Apr. 1992, v147–4, p356A.

C.C. Shulman, MD, PhD, "Section on Urology Program for Scientific Sessions", *The Journal of Urology*, Oct., 1992, p. 85.

Linda M. Kaairiki Shortliffe et al., "The Treatment of Urinary Incontinence by the Periurethral Implantation of Glutaraldehyde Dross–linked Collagen", *The Journal of Urology*, 1989 v141, pp. 538–541.

E. A. Balazs et al., *Marix engineering*1991, v2, pp. 173–178.

June Wilson et al., "Biomaterials for facial bone augmentation: Comparative studies",*Applied Biomaterials*, 1988, v22, (A2), pp. 159–177.

Larry L. Hench et al, "Bonding Mechanisms at the Interface of Ceramic Prosthetic Material",*J. Biomed, Mater, Res. Symposium*, 1971, v2, (part 1) pp. 117–141.

June Wilson et al., "Toxicology and biocompatibility of bioglasses", *Journal of Biomedical Materials Research*, 1981, v15, pp. 805–817.

Larry L. Hench et al., "Direct Chemical Bond of Bioactive Glass–Ceramic Materials to Bone and Muscle", *J. Biomed, Mater. Res. Symposium*, 1973, v4, pp.25–42.

*Primary Examiner*—Carlos A. Azpuru
*Attorney, Agent, or Firm*—Burns, Doane, Swecker & Mathis, L.L.P.

[57] ABSTRACT

The present invention relates to novel injectable aqueous suspensions of bio-active glass and dextrans for the repair of soft tissue or hard bone of mammals, especially in humans.

3 Claims, No Drawings

INJECTABLE BIO-ACTIVE GLASS IN A DEXTRAN SUSPENSION

This invention was made with government support under contract number F49620-92-JO351, awarded by a grant from the U.S. Air Force. The government has certain rights in the invention.

BACKGROUND OF THE INVENTION

It has been common practice in plastic, otolaryngological and other surgeries for many years to inject or place within tissues a variety of artificial substances to repair or reconfigure anatomic structures. For example, Teflon polytetrafluoroethylene) particles have been introduced into the vocal cords and more recently into periureteral and periurethral tissues with mixed results. Disadvantages associated with this procedure include long-term progressive foreign body reactions and migration and distant embolism associated with very small particles. Considerable research has been conducted to discover substitutes for Teflon and other conventionally employed artificial materials.

Bio-active glasses have been utilized as bone replacement materials in a variety of reconstructive surgical techniques. These glasses have been shown to develop a strong bond with hard tissue because of a series of ion exchange reactions between the implant surface and body fluids that result in the formation of a biologically active calcium phosphate film at the implant tissue interface. See Hench et al, *J. Biomed. Mater. Res.*, Vol. 5, pp. 117–141 (1971), and Hench et al, *J. Biomed. Mater. Res.*, Vol. 7, pp. 25–42 (1973). Bio-active glasses have also been shown to form a firm bond with soft tissue. See Wilson, et al, *J. Biomed. Mater. Res.*, Vol. 15, pp. 805–817 (1981); Wilson and Merwin, *J. Biomed. Mater. Res.: Applied Biomaterials*, Vol. 22, No. A2, pp. 159–177 (1988); and Wilson, Low et al, *Biomaterials and Clinical Applications*, Ed. By Pizzoferrato et al, Elsevier Science Publishers B. V., Amsterdam (1987).

Certain bio-active and bio-compatible glasses and glass-ceramics, e.g., those described in U.S. Pat. Nos. 4,159,358; 4,234,972; 4,103,002; 4,189,325; 14,171,544; 4,775,646; 4,857,046, and 5,074,916 (all incorporated herein by reference), have been shown to develop a unique, strongly adherent, chemical bond with hard tissue (bone) tissue due to the influence of hydroxyapatite formed from the biologically active calcium phosphate film generated in situ by ion-exchange reactions between the glass or glass-ceramic surface and body fluids. This influence results in a strong fixation of the glass or glass-ceramic to the bone surface. Although as noted above, a variety of such glasses have been shown to bond to various soft tissues, it has been found that several of these glasses result in the formation of an exceptionally thin (i.e., no more than about 1–3 fibers thick), but adherent collagen film which strongly adheres the glass to soft tissue without concomitant adverse side effects.

Failure to observe soft tissue bonding of some glasses was a consequence of inappropriate preparation of material and selection of inappropriate tissue sites, e.g., muscle. When the glass implant is successfully immobilized in appropriate soft tissue during the experimental period and when proper histological specimens are made, soft tissue adhesion to some glasses can be confirmed and evaluated. These particular glass compositions have also been found to advantageously become encapsulated with a thin (i.e., no more than about 1–3 fiber thick) layer of collagen after implantation.

It is an object of the present invention to provide a novel injectable composition and method for the repair, augmentation, reconfiguration or replacement of hard tissue (bone) or soft tissue anatomic structures which are not subject to disadvantages associated with presently employed materials.

SUMMARY OF THE INVENTION

The first aspect of the present invention is a pharmaceutically acceptable fluid composition capable of being injected via a surgical needle into an animal comprising a homogenous suspension of bio-active and bio-compatible glass particulate composition having particle size from about 250 $\mu$m to about 90 $\mu$m in an aqueous solution of dextrans or of dextran derivatives having an average molecular weight of about 10,000 to about $2 \times 10^6$ Daltons and optionally one or more preservative, coloring, flow enhancing, or suspension enhancing agents. This invention is particularly adapted for the repair, replacement, reconfiguration, reconstruction or augmentation of selected soft tissue and/or hard tissue (bone) anatomic structures. The ratio of particulate glass to the aqueous solution in the suspension is such that the fluid composition remains homogenous under pressures encountered during the injection and, following injection. The dextran is absorbed over time and the particulate glass remains at the selected anatomic structures and bonds uniformly throughout the particulate surfaces thereof with the soft tissue and/or hard tissue (bone) at the anatomic structures to provide anatomic integrity.

The second aspect is the reconfiguration, reconstruction or augmentation of selected soft tissue and/or hard tissue (bone) anatomic structures in a patient in need thereof comprising injecting into the soft tissue and/or hard tissue (bone) of the patient the fluid suspension of the first aspect.

DETAILED DESCRIPTION OF THE INVENTION

The term "fluid" as used herein means any flowable and injectable liquid composition, including highly viscous compositions sometimes referred to as "pastes."

As used herein, the term "animal" means mammal including a human. Unless specified otherwise the term "patient" means a human patient.

The term "Pharmaceutically acceptable" as used herein is consistent with the art and means compatible with the other ingredients of a pharmaceutical composition and not deleterious to the recipient thereof.

The term "surgical needle" means any needle adapted for delivery of the fluid compositions of the present invention into a selected anatomical structure.

The term "anatomic structure" refers to any site or locus composed of hard tissue (bone) and/or soft tissue within the body of an animal.

The term "anatomic integrity" refers to the desired size, shape or configuration of a particular anatomic structure after bonding therewith of the particulate glass phase of the composition of the present invention.

The term "homogenous" as used herein is intended to include all compositions (1) not subject to preferential extrusion of one or more of the components when injected into an animal and (2) not subject to segregation of one or more of the components of the mixture when allowed to stand for long periods of time.

Anatomic structures treatable according to the method of the present invention include, but are not limited to, vocal cords, periurethral tissue, periureteral tissue, maxilla, mandible, temporomandibular joint, chin, zygomatic arch, nose, ear, tooth root canal, tooth pulp caps, dental restoration, defects in bone, vertebral spaces, articulating joints, urethra, and subcutaneous and intradermal soft tissues.

As noted above in the discussion of the background of this invention, bio-active and bio-compatible material, especially ceramic and glass material, are known in the art of medicine as useful in the restoration of bone and soft tissue. This art is discussed extensively in *Introduction to Bioceramics,* Ed., L. L. Hench and J. Wilson, especially chapter 1, World Scientific, London (1993). The bio-active glass materials used in the present invention were selected on the basis that they:

(a) form a strong adherent bonds comprising a thin layer of collagen at a glass/soft tissue interface upon injection in the animal;

(b) form a strong adherent bonds comprising a layer of collagen no more than about 1–3 fibers thick;

(c) become encapsulated after injection in the animal with a collagen layer attached by chemical and mechanical bonding to the bio-active surface;

(d) do not after injection in the animal contribute to the formation of excess scar tissue, giant cells or acute inflammatory cells; and do not cause long lasting foreign body reactions.

Generally, it has been found that bio-active and bio-compatible glasses having the following weight percent compositions give satisfactory results when utilized as the particulate glass component of the invention.

| Component | Mole Percentage |
|---|---|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10 |

The bio-active particulate glass used in the present invention may be prepared according to the methods of the art such as taught in U.S. Pat. Nos. 4,159,358; 4,234,972; 4,103,002; 4,189,325; 54,171,544; 4,775,646; 4,857,046, and 5,074,916. For example, the raw materials (e.g., $SiO_2$, CaO, $Na_2O$ and $P_2O_5$) are mixed in Nalgene (trademark) plastic container on a ball mill for four hours. The mix is then melted in a platinum crucible at 1350° C. and homogenized for 24 hours. The molten glass is poured into distilled, deionized water to produce a glass frit. The frit is ground in a mortar and pestle and passed through ASTM sieves to produce the required particle size range.

Particles larger than 45 mesh ASTM Standard (355 μm) cannot be injected through a 16-gauge needle without unduly decreasing the volume of glass powder in the paste by a significant amount. Since the objective is to deliver as large a quantity of particles per injection as possible, the practical upper limit in particle size is about 355 μm.

Particles smaller than 90 μm are subject to macrophage attack in vivo. Since the objective is to retain the maximum number of particles in the tissues per injection, this establishes the lower limit of particle size at about 90 μm.

The following compositions of bio-active glasses are known by the trademark "Bioglass" licensed to US Biomaterials, One Progress Boulevard, #23, Alachua, Fla., 32615, have been found to yield particularly good results and are, therefore, preferred.

TABLE 1

Bioglass (Trademark) Bio-active Glass Compositions in Mole %

| Composition | $SiO_2$ | $Na_2O$ | CaO | $P_2O_5$ |
|---|---|---|---|---|
| 45S5 | 46.1 | 24.4 | 26.9 | 2.6 |
| 52S4.6 | 52.1 | 21.5 | 23.8 | 2.6 |
| 55S4.3 | 55.1 | 20.1 | 22.2 | 2.6 |
| 60S3.8 | 60.1 | 17.7 | 19.6 | 2.6 |

Dextrans are polysaccharides of D-glucose and are commercially produced by *Leuconostoc mesenteroides* and *L-dextranicum* bacteria. Dextrans have been widely used as plasma substitutes and blood extenders and are considered fully bio-compatible and are metabolizable. Dextrans are available in a wide range of average molecular weights varying from 4,000 to 40,000,000 Daltons and vary in rates of resorption in vivo from two to twenty days depending on the molecular weight. The use of dextran derivatives, such as dextran phosphate and sulfate, with bio-active glass is also within the scope of the present invention.

Dextrans and dextran derivatives useful in the present invention have molecular weights in the range of about 10,000 to about $2 \times 10^6$ Daltons preferably in the range of about 35,000 to about 150,000, and most preferably about 74,000.

In addition to bio-active glass, Dextrans or dextran derivatives, and sterilized deionized water, the composition of the present invention optionally contain excipients used in the pharmaceutical art to improve its performance and extend its shelf life. The excipients include, but are not limited to, preservative, coloring, flow enhancing, and suspension enhancing agents.

The fluid compositions of the present invention may be conveniently prepared by dissolving dextran in water (preferably sterile and deionized) to form a viscous solution suitable for injection. The ratio of dextran to water will vary according to the molecular weight of the dextran but will be in the range of about 50 g to about 150 g of dextran to 100 mL of water. The viscous aqueous dextran solution is mixed with bio-active glass particles in the ratio of about 35:65 to about 65:35% Wt. glass to dextran to form a fluid which is injectable.

Because the viscosity and, hence injectability, is a function of the ratio of glass to dextran, this ratio will vary according to application and the preference of the medical practitioner. The fluid composition is sterilized by heating at about 120° C. to 135° C. for a minimum of about 30 to about 60 min, cooled under sterile conditions, then stored under sterile conditions. The prepared fluid composition may be marketed in several viscosities. Further, the fluid can be thinned with sterile water according to the application and preference of the medical practitioner.

The fluid compositions of the present invention may be injected using a standard medical syringe and needle (16 to 22 gauge is typical) under the skin of a patient into an area of soft tissue or bone in need of repair or augmentation. The amount of composition injected is according to the professional judgement of the medical practitioner treating the patient. After injection, the dextran or the dextran derivative will begin to degrade and be removed from the site by phagocytosis. Degradation and removal will be essentially complete in about two to about twenty days depending on the molecular weight of the dextran. That is, lower molecular weight dextran degrades quicker than the high molecular weight dextran. The bio-active glass particles bond to the soft tissue site and create a long lasting augmentation of the tissue. In a hard tissue site the particles of glass will react and bond to existing bone and induce the formation of new bone which will infiltrate the site.

The following examples are offered as illustrations of the present invention and are not to be construed as limitations thereof.

EXAMPLE 1

Dextran of average molecular weight of about 74,000 to about 35,000 Daltons, 3.5 g is stirred into deionized water for injection, 5.0 mL to form a viscous solution. This dextran solution (5.0 mL) is then mixed with 5.0 cc, Bioglass (trademark) compostion 45S5, having particle size of about 125 μm to about 106 μm to form a 60:40 (dextran:bioactive glass) suspension of uniform consistency. This suspension is sterilized by heating at 125° C. for 30 minutes, cooled and stored in a pathogen free invironment. The sterile suspension is loaded into a sterile 3 cc syringe fitted with a 35 mm, 18 gauge needle (maintaining sterile conditions) and injected into subcutaneous soft tissue of a mouse.

EXAMPLE 2

An injectable suspension is prepared as in Example 1 except that benzyl alcohol is added as a preservative at the rate of 0.05% % by weight prior to storing under sterile conditions.

EXAMPLE 3

An injectable suspension is prepared as in Example 1 except that the composition of the bioactive glass is Bioglass 52S4.6:

EXAMPLE 4

The evaluation of dextran as an injectable vehicle was accomplished by injecting a series of different molecular weight dextrans ( 74,000, 150,000 and 2,000,000 Dalton supplied by Sigma Scientific, St. Louis, Mo.) and deionized water (Dl) to achieve a desired viscosity. This solution was then mixed with Bioglass (trademark) 45S5 particles and injected onto a glass microscope slide ten times through an 18 gauge needle using a 1 cc tuberculin syringe.

The following table summarizes the results of the evaluation of dextran for injectable systems:

TABLE 2

| MW Dextran | Wt. Dextran/ Vol DI $H_2O$ | Vol Dextran/ Vol Glass | Injectability of 1 cc (%) |
|---|---|---|---|
| 74,000 | 5.0 g./5.0 cc | 5.0 cc/5.0 cc | hard to inject 100% |
| 74,000 | 4.0 g./5.0 cc | 5.0 cc/5.0 cc | more easily inj. 100% |
| 74,000 | 3.5 g./5.0 cc | 5.0 cc/5.0 cc | easily inj. 100% |
| 150,000 | 4.0 g./5.0 cc | 5.0 cc/5.0 cc | did not inj. well <50% |
| 150,000 | 3.5 g./5.0 cc | 5.0 cc/5.0 cc | hard to inj. <80% |

The results show that the 74,000 Daltons dextran (3.5 gr in 5.0 cc deionized water) with a 50% by volume load of glass particles was injectable through an 18 gauge needle. This same mixture could not be reliably injected through a 19 gauge needle with the same 50% by volume load of glass particles. Injection through a 19 gauge needle is possible with similar mixtures of both glycerine and hylan as presented previously.

We claim:

1. A pharmaceutically acceptable fluid composition particularly adapted for the repair, replacement, reconfiguration, reconstruction or augmentation of selected soft tussue and/or hard tissue (bone) anatomic structures capable of injection via a surgical needle into an animal comprising a homogenous suspension of bio-active and bio-compatible glass particulate composition having particle size from about 250 μm to about 90 μm in an aqueous solution of dextrans or of dextran derivatives having an average molecular weight of about 10,000 to about $2 \times 10^6$ Daltons and optionally one or more preservative, coloring, flow enhancing, or suspension enhancing agents.

2. The pharmaceutical fluid composition of claim 1 wherein said bio-active glass is of the following composition:

| Component | Mole Percentage |
|---|---|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10 |

3. A method for repair, replacement, reconfiguration, reconstruction or augmentation of selected soft tussue and/or hard tissue (bone) anatomic structures in a patient in need thereof comprising injecting into said soft tissue and/or hard tissue (bone) of said patient a homogenous suspension of bio-active and bio-compatible glass particulate composition having particle size from about 250 μm to about 90 μm in an aqueous solution of dextrans or of dextran derivatives having an average molecular weight of about 10,000 to about $2 \times 10^6$ Daltons and optionally one or more preservative, coloring, flow enhancing, or suspension enhancing agents.

\* \* \* \* \*